(12) United States Patent
Wong et al.

(10) Patent No.: US 8,491,454 B2
(45) Date of Patent: Jul. 23, 2013

(54) SPINNING FORCE APPARATUS

(75) Inventors: Wesley P. Wong, Cambridge, MA (US); Kenneth A. Halvorsen, Natick, MA (US)

(73) Assignee: President and Fellows of Harvard College, Cambridge, MA (US)

(*) Notice: Subject to any disclaimer, the term of this patent is extended or adjusted under 35 U.S.C. 154(b) by 1000 days.

(21) Appl. No.: 12/326,279

(22) Filed: Dec. 2, 2008

(65) Prior Publication Data
US 2010/0137120 A1    Jun. 3, 2010

(51) Int. Cl.
*B04B 5/00* (2006.01)
*C12Q 1/68* (2006.01)
*G01N 33/53* (2006.01)

(52) U.S. Cl.
USPC ............ 494/10; 494/37; 494/85; 422/50; 422/400; 422/72; 435/7.1

(58) Field of Classification Search
USPC ...... 494/10, 37, 85; 422/50, 400, 72; 435/7.1, 435/7.21, 7.5, 7.6, 7.9
See application file for complete search history.

(56) References Cited

U.S. PATENT DOCUMENTS

| | | | |
|---|---|---|---|
| 6,654,102 B1 | 11/2003 | Modares et al. | |
| 7,052,650 B2 * | 5/2006 | Strick et al. | 422/50 |
| 2003/0166262 A1 | 9/2003 | Strick et al. | |
| 2007/0238598 A1 | 10/2007 | Kim et al. | |
| 2009/0118140 A1 * | 5/2009 | Suzara | 506/17 |

FOREIGN PATENT DOCUMENTS

| | | |
|---|---|---|
| EP | 0 123 178 | 10/1984 |
| EP | 0589556 A3 | 3/1994 |
| JP | 11 258081 | 9/1999 |
| WO | WO2008/112980 | 9/2008 |
| WO | 2010/065477 | 6/2010 |
| WO | 2011/153211 | 12/2011 |

OTHER PUBLICATIONS

Al Bitar et al., "Tarsal Morphology and Attachment Ability of the Codling Moth Cydia *Pomonella l.* (Lepidoptera, Tortricidae) to Smooth Surfaces," Journal of Insect Physiology, 55(11):1029-1038 (2009) XP026613479.
Federle et al., "Attachment Forces of Ants Measured with a Centrifuge: Better "wax-runners" have a poorer attachment to a smooth surface," Journal of Experimental Biology, 203(3): 505-512 (2000) XP002572371.

(Continued)

*Primary Examiner* — Michael Marcheschi
*Assistant Examiner* — Timothy Cleveland
(74) *Attorney, Agent, or Firm* — Wolf, Greenfield & Sacks, P.C.

(57) ABSTRACT

A spinning force system and methods of operation are provided for measuring a characteristic of a sample. The system includes a detection module having a light source for illuminating the sample and an objective being aligned to the light source to define a light path for producing an image of the sample. A rotor is mechanically coupled to the detection module and configured to rotate the light path for applying a force to the sample. The force may include a centrifugal force and other forms of force (such as a viscous drag force) resulted from the rotation. In some examples, the force is applied in a direction that is not parallel to a surface of the sample.

40 Claims, 10 Drawing Sheets

OTHER PUBLICATIONS

Salazar-Banda et al., "Determination of the Adhesion Force Between Particles and a Flat Surface, Using the Centrifuge Technique," Powder Technology, 173(2):107-117 (2007) XP022000669.

Chon et al., "A Von Willebrand Factor-derived heparin-binding peptide regulates cell-substrate adhesive strength and chemokinesis behavior," Biochemica et Biophysica Acta, Molecular Cell Research, 1542(1-3): 2002) XP004341335.

McClay et al., "Intercellular Recognition: Quantitation of Initial Binding Events," PNAS, 78(8): 4975-4979 (1981).

Koo et al., "Co-regulation of Cell Adhesion by Nanoscale RGD Organization and Mechanical Stimulus," Journal of Cell Science 115(7): 1423-1433 (2002).

M.S.Z. Kellermayer et al., "Folding-Unfolding Transitions in Single Titin Molecules Characterized with Laser Tweezers," Science, 276(5315):1112, 1997.

M. Rief et al.,"Reversible Unfold-ing of Individual Titin Immunoglobulin Domains by AFM," Science, 276(5315):1109, 1997.

M. Rief et al., "Single molecule force spectroscopy of spectrin repeats: low unfolding forces in helix bundles," Journal of Molecular Biology, 286(2):553{561, 1999.

A.D. Mehta et al., "Myosin-V is a processive actin-based motor," Nature, 400(6744):590{593, 1999.

S.M. Block et al., "Bead movement by single kinesin molecules studied with optical tweezers," Nature, 348(6299):348{352, 1990.

R. Merkel et al., "Energy land-scapes of receptor-ligand bonds explored with dynamic force spectroscopy," Nature, 397(6714):50{53, 1999.

E. Evans et al., " Chemically distinct transition states govern rapid dissociation of single L-selectin bonds under force," Proceedings of the National Academy of Sciences, p. 61324998, 2001.

C. Bustamante et al., "Ten years of tension: single-molecule DNA mechanics," Nature-London-, pp. 423{426, 2003.

K.C. Neuman and A. Nagy "Single-molecule force spectroscopy: optical tweezers, magnetic tweezers and atomic force microscopy," Nature Methods, 5:491{505, 2008.

F.J. Giessibl, "Advances in atomic force microscopy," Reviews of Modern Physics, 75(3):949{983, 2003.

K.C. Neuman and S.M. Block, "Optical trapping. Review of Scientifc Instruments," 75:2787, 2004.

D.G. Grier. "A revolution in optical manipulation," Nature, 424(6950):810{816, 2003.

E. Evans and K. Ritchie, "Dynamic strength of molecular adhesion bonds," Biophysical Journal, 72(4):1541{1555, 1997.

Julio M. Fernandez and Hongbin Li. "Force-Clamp Spectroscopy Monitors the Folding Trajectory of a Single Protein," Science, 303(5664):1674{1678, 2004.

G. Hummer and A. Szabo. "Free energy surfaces from single-molecule force spec-Troscopy," Acc. Chem. Res, 38(7):504{513, 2005.

M.T. Woodside et al., "Nanomechanical measurements of the sequence-dependent folding landscapes of single nucleic acid hairpins," Proceedings of the National Academy of Sciences, 103(16):6190{6195, 2006.

W.P. Wong. "Exploring single-molecule interactions through 3D optical trapping and tracking: from thermal noise to protein refolding" PhD thesis, Harvard University Cambridge, Massachusetts, 2006.

Noah Ribeck and Omar A. Saleh. "Multiplexed single-molecule measurements with magnetic tweezers.," Review of Scientifc Instruments, 79(9):094301, 2008.

A.M. van Oijen et al., "Single-Molecule Kinetics of Exonuclease Reveal Base Dependence and Dynamic Disorder. Science," 301(5637):1235{1238, 2003.

V. Heinrich et al., "Imaging Biomolecular Interactions by Fast Three-Dimensional Tracking of Laser-Con_ned Carrier Particles," Langmuir, 24(4):1194{1203, 2008. 10.

T. Ha. "Single-Molecule Fluorescence Resonance Energy Transfer. Methods," 25(1):78{86, 2001.

Friedrich et al., The slow rotating centrifuge microscope NIZEMI—a versatile instrument for terrestrial hypergravity and space microgravity research in biology and materials science. J Biotechnol. Jun. 27, 1996;47(2-3):225-38.

Halvorsen et al., Massively parallel single-molecule manipulation using centrifugal force. Biophys J. 2010 Jun 2;98(11):L53-5.

Harvey et al., A microscope-centrifuge. Science. Jul. 11, 1930;72(1854):42-4.

Monroe, The optical trap. Scientist. Aug. 29, 2005;19(16):48-52. Retrieved from the internet http://www.the-scientist.com/?articles.view/articleNo/16665/title/The-Optical-Trap/ on Jan. 28, 2013.

Tarsa et al., Detecting force-induced molecular transitions with fluorescence resonant energy transfer. Angew Chem Int Ed Engl. 2007;46(12):1999-2001.

Vargas et al., A centrifuge for studies of fluid dynamics phenomena in a rotating frame of reference. Revista Mexicana de Fisica. Jun. 2002;48(3):255-266.

* cited by examiner

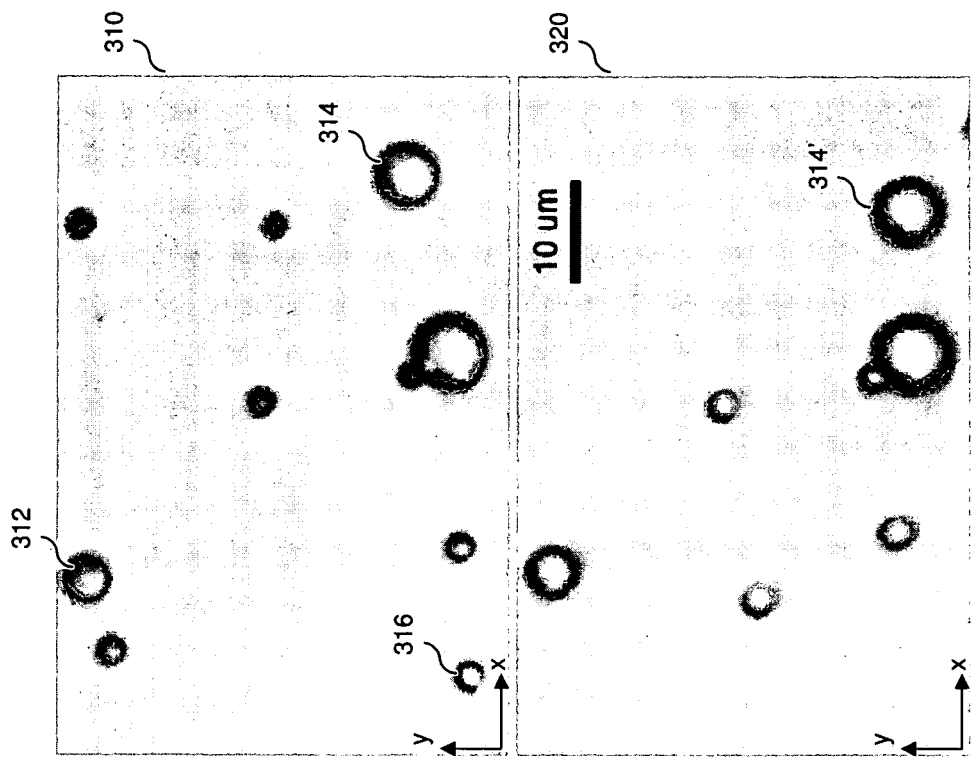

Interference patterns

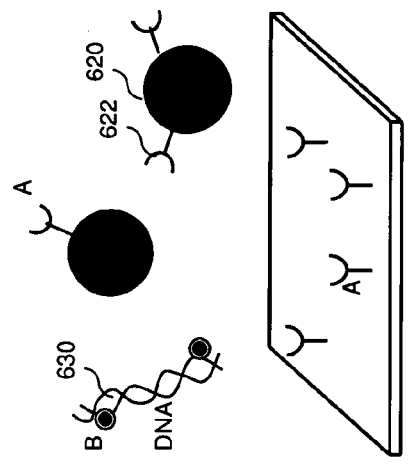
FIG. 6B
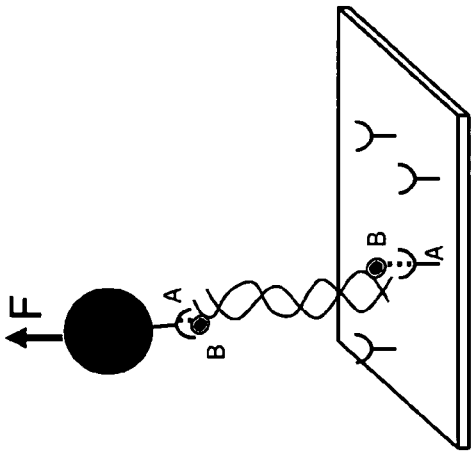
FIG. 6D
FIG. 6A
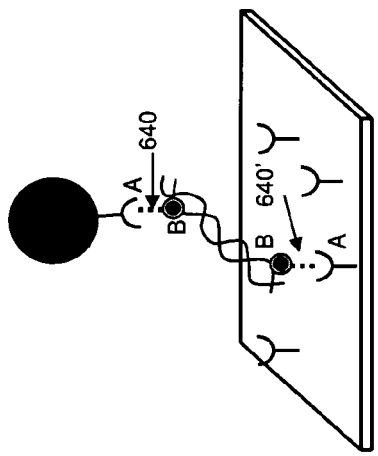
FIG. 6C

SPINNING FORCE APPARATUS

BACKGROUND

This invention relates to measurement of forces relating to molecules.

The ability to quantify interactions between biomolecules is of great interest for scientific and medical research, as well as for drug development. Examples of measurable characteristics of a biomolecular interaction include the affinity (e.g., how strongly the molecules bind/interact) and the kinetics (e.g., rates at which the association and dissociation of molecules occur) of the interaction. Traditionally, such characteristics are measured in solution, using methods such as calorimetry, stop-flow imaging, or surface plasmon resonance. These bulk measurements are limited in many ways, including 1) they report only average behavior and thus may lose important details associated with metastable states and rare events, and 2) they measure chemistry in the absence of externally applied mechanical stress, which can be dramatically different from crowded and dynamic environments in living systems.

Recent development in single molecule measurement methods offers a different approach in quantifying molecular interactions by examining the behavior of individual molecules rather than measuring the properties of bulk solutions. This approach enables the observation of rare or fleeting events that can be obscured by ensemble averaging. The resulting detailed information of molecular transitions helps researchers to identify metastable states and to study the transitions rates and the chemical pathways between such states. Furthermore, heterogeneities between molecules in a population and within the behavior of a single molecule can both be quantified.

Currently, force probes that apply single molecule measurement methods include atomic force microscopes (AFM), optical traps, magnetic tweezers, biomembrane force probes, and flow chambers. Despite many advantages, these devices still have several limitations. For example, due to technical complexities, some systems require a large investment of money and time (e.g. optical trap systems typically cost $150 k or more). Additionally, molecular interactions are studied one molecule at a time in most cases. Statistical characterization of these interactions is therefore slow and painstaking, requiring hundreds or thousands of measurements which are typically performed in a serial manner.

SUMMARY

One general aspect of the invention provides a method for rotating an object attached to a surface of a substrate. The substrate is coupled to a rotary member. The rotary member is rotated to apply a force to the object in a direction that is not in parallel to the surface of the substrate. A light source illuminates the surface of the substrate. A relative motion of the object to the surface of the substrate caused by the force is detected using a detector.

Embodiments of this method may include one or more of the following features.

The force applied to the object may have a force component in a direction perpendicular to the surface of the substrate. The force may include a centrifugal force. When the object is in contact with a liquid medium, the force may also include a viscous drag force.

A magnitude of the force applied to the object may be controlled, for example, by changing an angular velocity of the rotary member or by changing a distance of the object to a center of the rotation. The direction of the force applied to the object may also be controlled, for example, by changing an orientation of the substrate relative to the rotary arm.

The light source and/or the detector may be rotated at an angular velocity substantially the same as that of the rotary member. The rotary member may be rotated about an axis substantially parallel to the surface of the substrate.

The relative motion of the object to the surface of the subject may be sufficient to detach the object from the surface of the substrate.

A magnitude of a force interaction between the object and the surface of the substrate may be determined based on the magnitude of the force applied to the object by the rotation.

The object may include a molecule. The relative motion of the object may include a motion indicative of a conformational change of the molecule. The conformational change may include unfolding, refolding, stretching, and/or relaxing of the molecule. The relative motion of the object may also include a motion indicative of a rupture or a formation of a bond at least partially associated with the molecule.

An image of the object may be generated with the detector, and a change in the image may be determined. The image may include a transmitted light image, a reflected light image, and/or a fluorescence image.

The detector may include a light detector, which may be a charge-coupled device or a CMOS detector.

The object may include a biological subject such as a molecule, a cell organelle, a cell, or a tissue. The object may further include a carrier that forms a chemical linkage with the biological subject. The carrier may be a bead.

The object may include a first molecule, and the surface may include a second molecule for forming an interaction with the first molecule. The first molecule may be a receptor and the second molecule may be a ligand of the receptor.

The object may include a group of individual targets attached to the surface of the substrate. The force applied to the object may include a corresponding group of force components each applied to a respective one of the individual targets.

Another general aspect of the invention provides a method including: attaching a particle to a surface of a substrate through a molecular interaction associated with a first molecule and second molecule; rotating the substrate to apply a force to the particle in a direction that is not in parallel to the surface of the substrate; detecting an image of the particle with a detector, the image containing information representing a characteristic of the molecular interaction; and determining the characteristic of the molecular interaction based on the detected image.

Embodiments of this method may include one or more of the following features.

The method may further include determining a relative motion of the particle to the surface of the substrate. The relative motion may include detachment of the particle from the surface of the substrate, a motion indicative of a rupture or a formation of a chemical bond associated with the molecular interaction, or a motion indicative of a conformational change of at least one of the first and the second molecules. The conformational change may include unfolding, refolding, stretching and/or relaxing of at least one of the first and second molecules.

Determining the characteristic of the molecular interaction may include measuring a strength characteristic of the molecular interaction and/or measuring a kinetic characteristic of the molecular interaction. The kinetic characteristic of the molecular interaction includes an association rate $K_{on}$ or a dissociation rate $K_{off}$ of the molecular interaction.

A first chemical linkage may be formed between the particle and the first molecule. A second chemical linkage may be formed between the second molecule and the surface of the substrate.

The method may further include controlling a rotation of the substrate such as controlling an angular velocity of the rotation of the substrate.

The first molecule may be a receptor and the second molecule may be a ligand of the receptor. Alternatively, the first molecule may include a first molecular complex, and the second molecule may include a second molecular complex that interacts with the first molecular complex. The first molecular complex may include one or more receptor-ligand pairs.

The particle may include a bead. The bead may have a diameter in the range between 1 nm and 1 mm, and a density in the range between 0.01 g/cm$^3$ and 20 g/cm$^3$.

Another general aspect of the invention provides an apparatus for measuring a characteristic of a sample. The apparatus includes a detection module having a light source for illuminating the sample and an objective being aligned to the light source to define a light path for producing an image of the sample. A rotor is mechanically coupled to the detection module and configured to rotate the light path for applying a force to the sample.

Embodiments of this apparatus may include one or more of the following features.

The detection module may further include a sensor for detecting the image of the sample and for generating electrical signals representative of the image. The sensor may include a light detector. The light detector may include a charge-coupled device.

The sensor may be rotated by the rotor at an angular velocity the same as that of the light path. Alternatively, the sensor may be stationary to a ground, in which case a rotating mirror may be provided for directing a light signal of the image generated by the objective to the sensor.

A positioner may be coupled to at least one of the objective and the light source. The positioner may be configured to adjust a relative position of the objective to the light source.

A sample housing may be provided for mounting the sample to the detection module. A positioner may be coupled to the sample housing. The positioner may be configured to adjust a configuration of the sample housing to change an orientation of the sample, or to adjust a relative position of the sample housing to the objective at least in a direction of the light path. The positioner may be further configured to adjust the relative position of the sample housing to the objective in each of three orthogonal directions.

A data transmission module may be coupled to the sensor. The data transmission module may be configured to transmit the electrical signals representative of the image to be processed. The data transmission module may include a first media converter for converting the electrical signals to optical signals, a second media converter for converting the optical signals to subsequent electrical signals to be processed, and an optical fiber for transmitting the optical signals from the first media converter to the second media converter.

A rotor controller may be coupled to the rotor. The rotor controller may be configured to provide a control signal for controlling the rotation of the light path, or alternative, for controlling an angular velocity of the rotation of the light path.

A detection controller may be coupled to the detection module for providing a control signal to change an optical characteristic of the detection module. The optical characteristic may include an illumination intensity of the light source, a light frequency of the illumination of the light source, and/or an image acquisition characteristic of the sensor.

Among other advantages and features, the spinning force system and methods described herein can provide one or more of the following advantages.

The system and methods of operation can provide massively-parallel high-throughput single-molecule force measurements at a low cost. More specifically, rotation-induced forces (e.g., centrifugal forces and viscous drag forces) can be used to manipulate single molecules (e.g., proteins or DNAs) or molecular complexes (e.g., receptor-ligand protein pairs), enabling forces to be applied simultaneously to many subjects. Each subject can be observed directly and independently for true single-molecule detection.

The system and methods of operation can provide accurate force control in a wide range of directions and magnitudes. Through force control, the system and methods of operation can be used to quantify force dependent interactions, including measuring the force dependence of kinetic parameters (e.g., $K_{on}$ and $K_{off}$) and molecular subtleties which would be invisible from population averaging. Using this system, the mechanical properties of biomolecular complexes (e.g., compliances of DNAs and proteins) and cellular targets (e.g., elasticity of stress-bearing cells) can be studied, yielding valuable information into both the structure and the function of those subjects.

The system and methods of operation can be conveniently integrated with various types of force probes to generate forces in multiple dimensions with high flexibility. For example, the system can be used in conjunction with optical traps, magnetic tweezers and/or microfluidic devices to generate a combination of forces (such as gradient and scattering forces, magnetic forces, hydrodynamic forces, and centrifugal forces). Each force can be applied to a sample in a different direction, with a different magnitude, and/or at a different test stage.

The system and methods of operation can also be conveniently integrated with various imaging techniques to provide real-time observation with high temporal and spatial resolution. For example, using interference techniques and diffraction analysis, the position of individual particles in a sample can be ascertained with sub-nanometer accuracy. Also, fluorescent imaging enables visualization of subtle molecular transitions during experiment. Moreover, using video tracking by high-speed CCD cameras, molecular events can be detected on the scale of microseconds.

Other features and advantages of the invention are apparent from the following description, and from the claims.

BRIEF DESCRIPTION OF DRAWINGS

FIGS. 3A and 3B are transmitted light images of a sample generated at two different focal depths, respectively.

FIGS. 6A-6D are schematic representations of another procedure for preparing a sample to be measured by the spinning force system of FIG. 1.

DETAILED DESCRIPTION

1 System Overview

Figure 1:
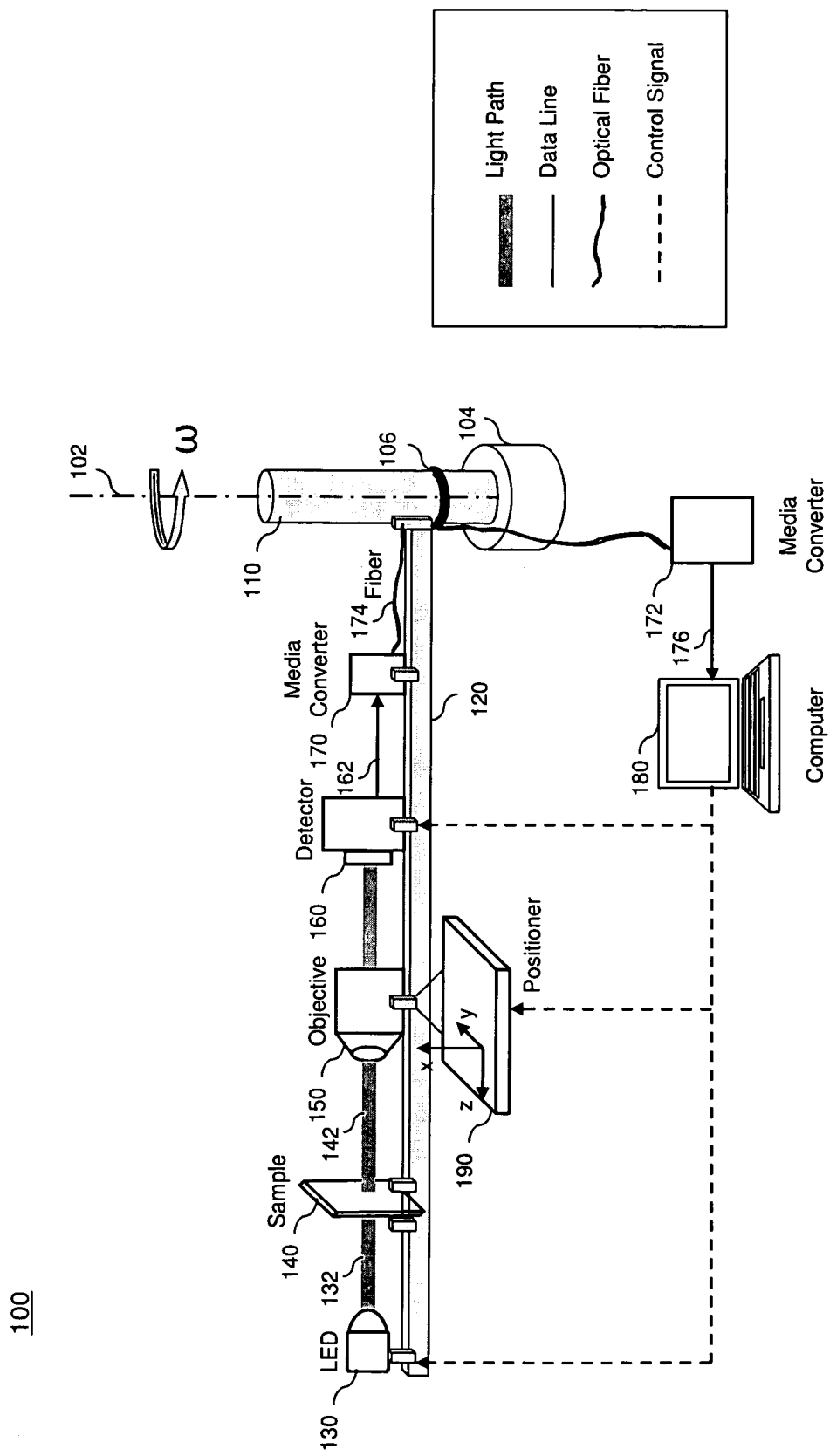
FIG. 1 is a schematic representation of one embodiment of a spinning force system.

Referring to FIG. 1, a spinning force system 100 includes a rotary arm 120 mechanically coupled to a rotary stage 110 configured to rotate about a central axis 102 at an adjustable angular velocity ω. Rotary stage 110 is housed and supported on a stationary base 104 immobilized on a platform (not shown) such as a vibration-free optical table.

Rotary arm 120 extends radially outward from central axis 102 to support a set of optical, mechanical, and electrical components for detecting characteristics (e.g., motion, optical, and geometric characteristics) of a sample 140 to be measured by system 100. These components include, for example, a light source 130, an objective 150, a light detector 160, and a media converter 170. In operation, these components are moved by rotary arm 120 to rotate about central axis 102 at the same angular velocity ω. Rotary arm 120 may also carry one or more positioning elements (e.g., adjustment screws and electromechanical stages such as piezoelectric positioners) for adjusting the position of each component coupled to arm 120. Examples of positioning elements will be described in greater detail below.

In this example, light source 130 is mounted at a distal end of rotary arm 120 for emitting a light beam 132 to illuminate a selected region of sample 140. Examples of light source 130 suitable for use in system 100 include various types of lamps (such as LED bulbs and xenon arc lamps) and lasers (such as single- and multiple-wavelength lasers). Light source 130 may also include a set of optical components such as lenses, mirrors, and filters (not shown) for controlling the characteristics of its outgoing beam 132. For example, a condenser with diaphragms may be used for tuning the emission intensity of beam 132, and a color filter may be used for transmitting light at only selected wavelengths.

Sample 140 is mounted onto rotary arm 120 with a sample holder (not shown) fastened to the arm. Depending on the particular implementation, sample 140 may include a sample chamber (not shown) in which experiment subjects (such as cells, biomolecules, and DNA strands) are sealingly contained. The sample chamber may consist of two parallel cover glasses separated by a 1 mm o-ring, forming an enclosed volume that can be filled with buffer and beads. In some implementations, sample 140 is oriented such that the surfaces of the cover glasses are aligned in parallel to central axis 102. When rotary arm 120 rotates, the contents of sample 140 experience a centrifugal force normal to the cover glasses. In other implementations, sample 140 is oriented at a selected (and possibly adjustable) angle with respect to central axis 102, enabling the centrifugal force to be applied in any given direction.

Light beam 142 exiting sample 140 is received by objective 150 to produce a real image of the illuminated region of sample 140. The optical characteristics of objective 150 (e.g., magnification and numerical aperture) are selected depending on the particular implementation. For example, a 20× air-immersion objective may be used for applications that require a wide field of view, whereas a 100× oil-immersion objective may be preferred for applications that require a high spatial resolution.

Preferably, the relative position of objective 150 with respect to sample 140 is adjustable in three dimensions (x-, y- and z-directions shown in the figure), allowing images of different regions of the sample to be collected at various focal depths. In this example, objective 150 is staged on a piezo-electric positioner 190, which can be translated along each of the x-, y-, and z-directions by an external control signal (e.g., provided by a computer). In other examples, sample 140 (instead of objective 150) may be staged on positioner 190 for linear translation in those three dimensions.

Images formed by objective 150 are received by detector 160 and subsequently converted into electronic signals 162. One example of a detector suitable for use is a charge-coupled device (CCD), such as a 12-bit 512 pixels×512 pixels CCD camera. Another example of a suitable detector is a CMOS detector. Preferably, detector 160 is capable of acquiring successive images at a speed sufficiently fast to enable video tracking of sample 140 at a high temporal resolution (e.g., 1 kHz). In some examples, light from objective 150 is first transformed through an intermediate optical system (not shown) before reaching detector 160. The intermediate optical system may include one or more elements such as lenses, filters, polarizers, and pinholes.

Electronic signals 162 from detector 160 are delivered, for example, using electrical, optical, or wireless transmission means, to be passed onto a computer 180. In this example, signals 162 are transmitted sequentially through an electronic-to-optical media converter 170, an optical fiber 174, and an optical-to-electronic media converter 172. Both media converter 172 and computer 180 are positioned on a stationary platform (not shown). Optionally, optical fiber 174 is coupled to rotary stage 110 through a fiber optic rotary joint (not shown), which can be further integrated into an electrical slipring 106 of rotary stage 110. Using proper interfacing software, computer 180 decodes electronic signals 176 from media converter 172 to reproduce images of sample 140 on a screen.

Computer 180 is used for viewing and processing images of sample 140. In addition, computer 180 is also configured to provide various control signals to control individual components of spinning force system 100. For example, computer 180 may be coupled to an electric motor (not shown) for controlling a rotational drive force to change the angular speed a) of rotary stage 110. Computer 180 may also be coupled to a positioning device (not shown) for adjusting a distance between light source 130 and sample 140, or coupled to positioner 190 for translating objective 150 in each of x-, y-, and z-directions to select detection regions and to control focal depth. Computer 180 may also be configured to control the optical characteristics of light source 130 (e.g., the brightness and the frequency range of output beam 132) as well as the image acquisition variables of detector 160 (e.g., readout rate, integration time, and electronic gain). Additionally, computer 180 may provide control signals based on previously acquired data, enabling real-time feedback control.

2 Operation

2.1 Force Application

Figure 2B:
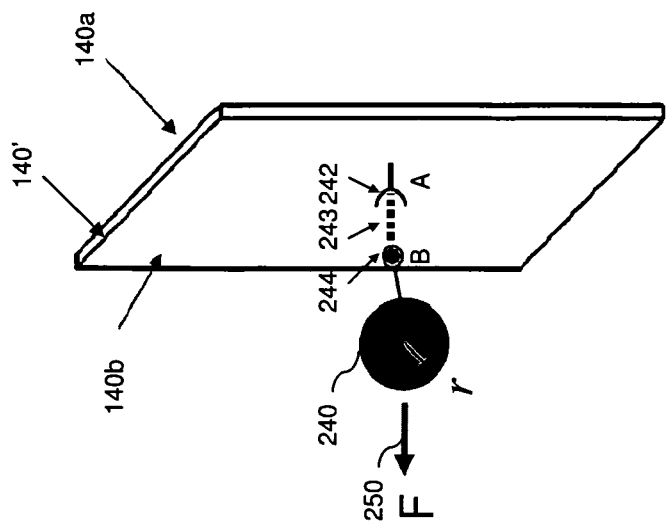
FIG. 2B shows a centrifugal force applied to the sample of FIG. 2A.
Figure 2A:
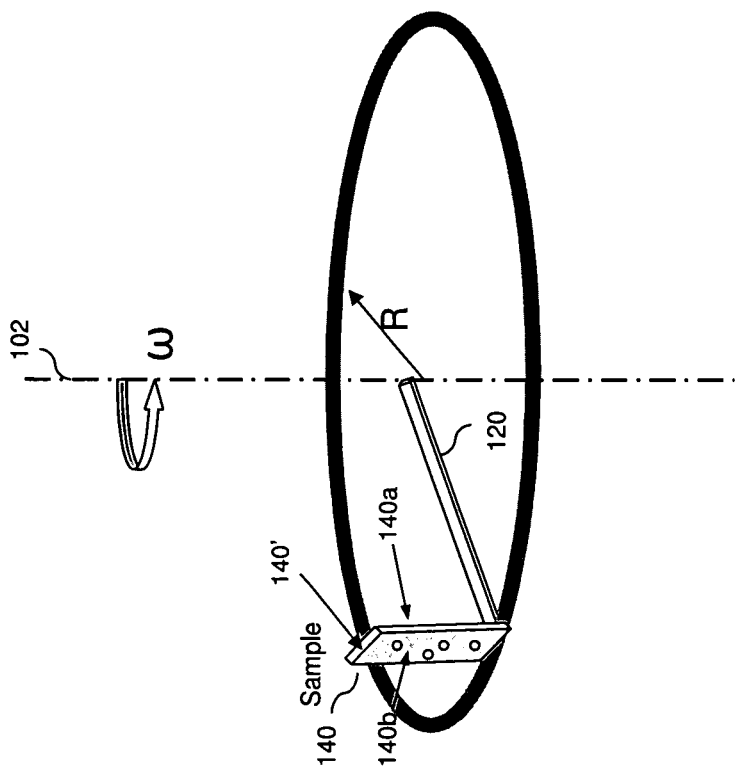
FIG. 2A is a schematic representation of a sample coupled to the spinning force system of FIG. 1.

Referring to FIGS. 2A and 2B, when rotary arm 120 is in operation, sample 140 rotates at an angular velocity ω and at a distance R from the center of axis 102. For illustrative purposes, in this example, sample 140 includes a cover slip 140' having an inner surface 140a and an outer surface 140b with respect to axis 102. Both surfaces are aligned in parallel with axis 102. A particle 240 (e.g., a bead) adheres to outer surface 140b through a chemical bond 243 formed between molecule A 242 and molecule B 244. In this example, molecule A is a receptor chemically linked to outer surface 140b, and molecule B is a ligand chemically linked to particle 240. (The techniques and methods for forming such linkages will be described in greater detail below).

When particle 240 undergoes circular motion, a centripetal force F is exerted on the particle, as defined by the following equation:

$$F = \frac{mv^2}{R} \quad (1)$$

where F is the net centripetal force, m and v are the mass and the linear velocity of the particle, respectively, and R is the distance of the particle from rotation axis 102. In a rotating reference frame in which orbiting particle 240 appears stationary, particle 240 experiences an inertial centrifugal force equal to F in a direction perpendicular to outer surface 140b and away from central axis 102 (shown by arrow 250). In some examples where particle 240 is a spherical bead in solution with radius r and relative density ρ, rewriting equation (1) in terms of angular velocity ω yields:

$$F = \frac{4\pi \rho r^3 R \omega^2}{3} \quad (2)$$

When sample 140 rotates about axis 102 at a very low speed, centrifugal force F is countered by the interaction force of chemical bond 243, allowing particle 240 to continue to adhere to surface 140b. As the rotational speed ω rises, the increasing magnitude of centrifugal force F causes bead 240 to move with respect to surface 140b. The characteristics of the relative motion (e.g., the root-mean-square displacement or the direction of the motion) can be monitored and analyzed to quantify certain chemical and/or mechanical properties of bond 243 (e.g., properties associated with its transitional states and conformational changes). The increasing F may also cause the rupture of chemical bond 243, at which point, particle 240 is released from surface 140b. The magnitude of centrifugal force F at the particle release indicates the rupture force of chemical bond 243.

During operation, the magnitude of centrifugal force F can be controlled, for example, by adjusting the angular velocity ω of rotary arm 120. For instance, sample 140 can be subjected to multiple cycles of force application in which the centrifugal force on particle 240 is increased and/or decreased through step changes in angular velocity ω.

In addition to changing the angular velocity ω, it is also possible to change the radius of rotation R either statically or dynamically by changing the sample position relative to the axis of rotation. For example, in system 100, sample 140 may be mounted to an adjustable rotary arm with extendible length, or staged on a positioner that can be translated in a radial direction with respect to central axis 102.

In cases where particle 240 is a spherical bead, the centrifugal force F can also be varied by changing one or more of the particle characteristics ρ and r shown in equation (2). For example, microspheres are commercially available in a wide range of materials and sizes (see Table 1 below). By conjugating subjects of study (e.g., molecules or cells) to selected microspheres, the centrifugal force applied to the microspheres (and translated to the subject) can be varied based on bead properties. In addition, the degree of monodispersity of beads can control the range of forces applied for a given spin. For instance, a highly monodisperse sample (e.g., using beads of substantially the same size and properties) may cause all beads to experience the same force, while a polydisperse sample (e.g., using beads of various sizes and/or properties) would have a wide range of forces being applied. Moreover, ρ of particle 240 can also be altered by changing the density of the buffer solution. Furthermore, the geometry of the sample chamber can be varied to control the effects of fluid flow, which can add hydrodynamic forces to immobilized particles in the chamber.

TABLE 1

The materials and sizes of common beads

| Bead Material | Specific Density (g/cm³) | Size Range (μm) |
|---|---|---|
| Borosilicate | 1.5 | 1-100+ |
| Polystyrene | 0.05 | 0.05-100+ |
| Silica | 1.2 | 0.01-100 |
| Gold | 18.3 | 0.002-0.25 |
| Melamine | 0.51 | 0.5-10 |
| Iron Oxide | 4.24 | 1-10 |

With proper parameter selection, the force applied to particle 240 can span 9 orders of magnitude, ranging from microNewtons (e.g., r=10 μm, ρ=1.5 g/cm³, R=500 mm, ω=100 Hz) to femtoNewtons (e.g., r=1 μm, ρ=0.05 g/cm³, R=250 mm, ω=2 Hz).

The direction of the centrifugal force F can also be controlled. In some examples, sample 140 may be configured in an orientation perpendicular to rotational axis 102, resulting in a centrifugal force F along surface 140b. In other examples, sample may be configured to form a selected angle with respect to rotational axis 102 so that centrifugal force F may be applied in any given direction. For instance, a compressive (rather than tensile) force can be applied to particle 240 if the particle is positioned on inner surface 140a (rather than outer surface 140b) of the cover glass. For particular implementations, it may be desirable to place sample in a parallel position with respect to rotation axis 102 because pulling particle 240 away from surface 140b reduces the likelihood of the particle forming new interactions with unoccupied binding sites of molecule A on the surface 140b.

In addition to centrifugal force F, other types of forces can also be applied to particle 240 through spinning. For example, if particle 240 is contained in a chamber filled with a liquid medium, the rotation of sample 140 can generate regional flows that exert a viscous drag force D to particle 240. The direction of the drag force depends on factors such as the geometry of the chamber and the orientation of the sample. The magnitude of the drag force depends on factors such as the viscosity and the temperature of the liquid medium, the size of the particle, and the rotational velocity and acceleration of the sample.

2.2 Observing Motion Characteristics

In spinning force system 100, motion of particle 240 (e.g., displacement caused by molecular folding, unfolding or rupture of bond 243) can be observed by video tracking methods (e.g., by taking successive images of the particle at a high temporal resolution). Because light source 130, sample 140 and objective 150 rotate together at the same angular velocity ω, these three components appear stationary to each other in a rotating reference frame. Therefore, images of particle 240 can be formed using traditional imaging techniques, including transmitted- or reflected-light techniques and fluorescence techniques.

Referring to FIGS. 3A and 3B, images 310 and 320 are transmitted-light images of the same region of sample 140 produced at two different focal depths, respectively. In this example, sample 140 contains multiple beads (appearing, for example, as circular objects 312, 314 and 316 in image 310) near surface 140b. The location of each bead in the images represents the lateral position of the bead (e.g., along x- and y-axes of FIGS. 1, 3A and 3B). The image pattern of the bead (e.g., the size, the sharpness and the ring pattern of circular objects 312, 314 and 316) indicate the focal depth, namely, the distance of the bead from objective 150 (e.g., along z-axis of FIG. 1). This focal depth can be used to represent the relative position of the bead above surface 140b.

By analyzing the lateral position and the image pattern of individual beads, the movement of the beads with respect to time can be characterized in a three-dimensional space. Such characterization enables the quantification of the affinity and the kinetics of chemical bond 243 that links the bead to surface 140b. For example, before spinning, the position of objective 150 can be adjusted such that particle 240 situates in the objective's focal plane, resulting in a sharp in-focus image when the particle adheres to surface 140b. During spinning, if the centrifugal force F is sufficiently strong to cause bond rupture, particle 240 is quickly (typically at a speed of microns/s or faster) pulled away by centrifugal force F from surface 140b (e.g., along z-axis of FIG. 1). The escape of the particle from the objective's focal plane can be observed by changes in the characteristics of the detected image that are correlated with changes in focal depths. For example, a disappearance or blurriness of a circular pattern representing particle 240 (e.g., similar to the disappearance of object 316 from image 320 or the blurriness of object 314' in image 320) indicates that the particle is being pulled away from the focal plane of objective 150, e.g., as a result of bond rupture. Once bond rupture is identified, the bond force can be computed based on the magnitude of centrifugal force F, as defined in equation (1) or (2).

In examples where bond rupture is not necessarily observed or desired, detecting particle movement can provide valuable information about the compliance of a molecular tether that includes bond 243. For example, the displacement of particle 240 subjected to varying amplitude of centrifugal force F can be used to compute the elastic modulus of the molecular tether, and possibly to map the force dependency of such modulus. Also, stepwise changes in the position of particle 240 may indicate the transitions between molecular states that are associated with conformational changes of a chemical bond. For example, a bead that remains tethered but moves suddenly away from the cover glass can signify unfolding of a protein domain.

The transmitted light imaging technique described above can easily provide a spatial resolution along the optical axis of about 100 nm for observation. In certain implementations where a higher resolution is desirable, more sophisticated imaging and image processing techniques can also be applied. For example, by using advanced techniques such as using transmitted or reflected light interference patterns of individual beads, the position of a bead relative to surface 140b can be determined with sub-nanometer accuracy.

Figures 4A, 4B, 4C:
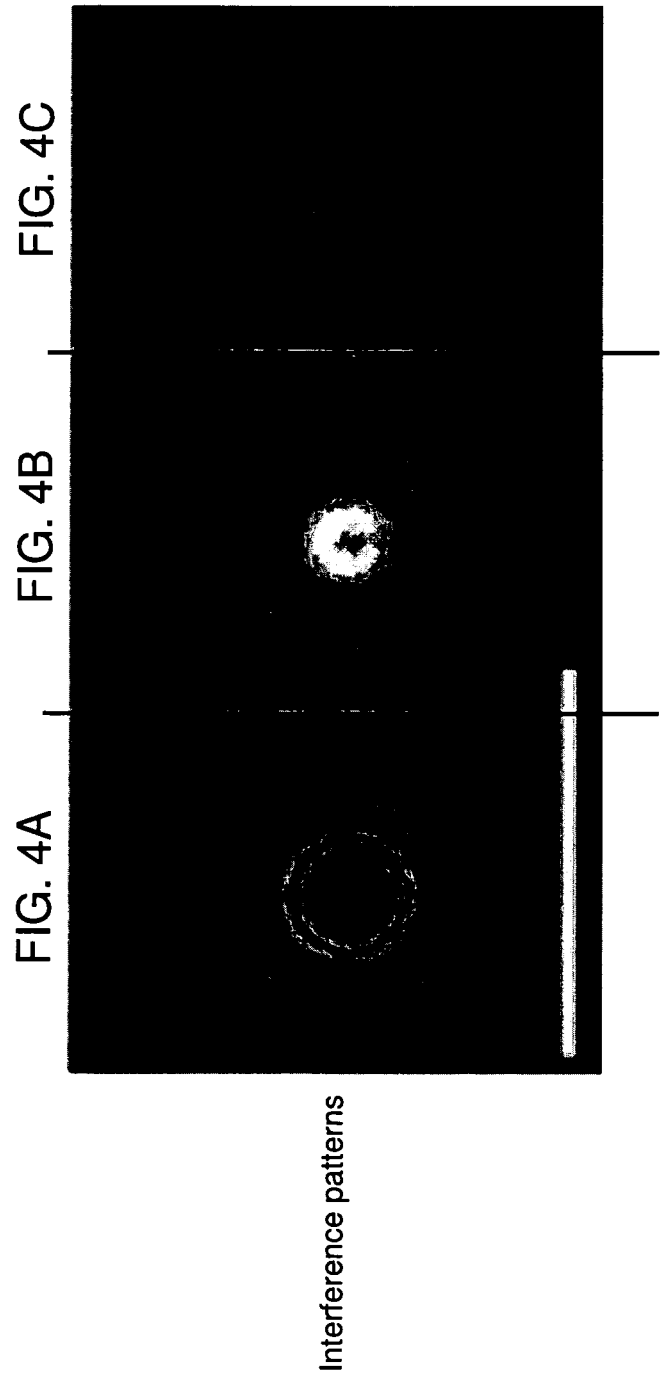
FIGS. 4A-4C show the interference patterns of a sample imaged by a reflection interference contrast microscope at three different heights, respectively.

Referring to FIGS. 4A-4C, the interference patterns of a single particle imaged by a reflection interference contrast microscope (RICM) at three different heights are shown, respectively. In these figures, the alternation of dark and bright fringes as well as the intensity and the size of each fringe can be decoded to reconstruct the height profile of the particle with a sub-nanometer axial resolution. (The white bar shown in these figures represents 10 μm). An example of particle tracking using the RICM technique is described by Heinrich et al., in Fast Three-Dimensional Tracking of Laser-Confined Carrier Particles, published in *Langmuir*, 24(4): 1194-1203, 2008, the contents of which are incorporated herein by reference.

In addition to the aforementioned imaging techniques, fluorescence techniques can also be implemented alone or together with transmitted/reflected light techniques to enhance resolution and to enable visualization of subtle molecular transitions during experiment.

3 Applications

Using the centrifugal force (and possibly other forces) of a spinning sample, spinning force system 100 is capable of performing single-molecule experiments for application in a wide range of areas, including receptor-ligand interactions, DNA mechanics, the kinetics of motor proteins, and the dynamics of intramolecular transitions such as protein folding and unfolding. In addition, spinning force system 100 can also be used for high-throughput molecular screening in which thousands of single-molecule experiments of the same or different types can be performed in parallel and/or in series. This can be particularly useful for drug discovery and screening. The following section provides several scenarios in which spinning force system 100 is useful.

3.1 Example I

One application of spinning force system 100 relates to studying the molecular interactions between two or more interacting molecules or molecular complexes, including, for example, measuring the association rate $K_{on}$ and dissociation rate $K_{off}$ of the interaction, identifying metastable states, and determining the transition rates between such states. Examples of interacting molecules suitable as subject of study include receptor-ligand pairs, such as biotin-streptavidin, antibody-antigen, enzyme-substrate, and DNA-polymerase.

Referring to FIGS. 5A-5D, one procedure of preparing a sample containing two interacting molecules A (e.g., biotin) and B (e.g., streptavidin) for measurement is illustrated.

Figure 5B:
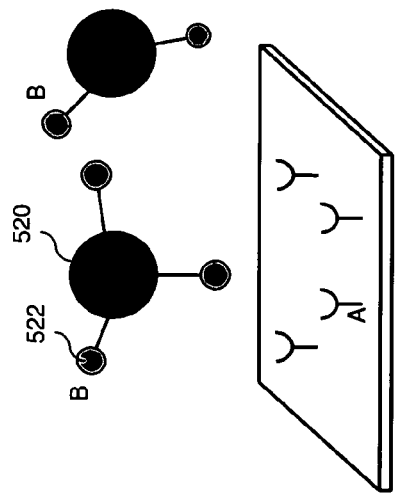
FIGS. 5A-5D are schematic representations of a procedure for preparing a sample to be measured by the spinning force system of FIG. 1.
Figure 5D:
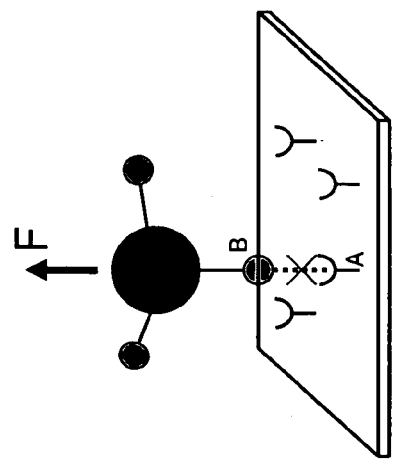
Figure 5A:
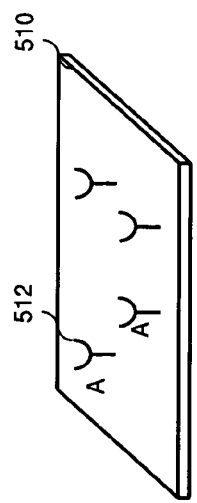

For example, in FIG. 5A, a cover glass 510 is coated with a dispersed layer of molecule A 512 using proper functionalization techniques such as physisorption or covalent linkage.

In FIG. 5B, a solution of glass beads 520 is then added onto cover glass 510. Each bead is pre-coated with one or more molecules B 522, again using proper functionalization techniques.

Figure 5C:
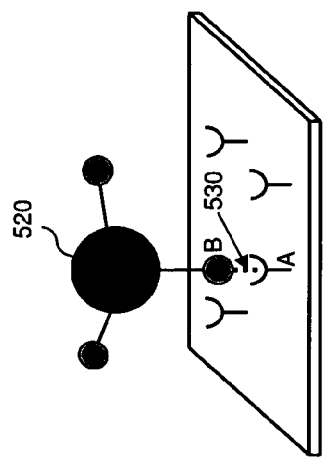

In FIG. 5C, cover glass 510 is incubated with glass beads 520 to enable formation of interaction 530 between molecules A and B. Consequently, some beads 520 become attached to the surface of cover glass 510 through newly formed interactions 530. Unattached beads can be removed from the surface by rinsing with an inactive solution, or alternatively, removed by a centrifugal force applied during measurement. In some examples, the amount of interactions 530 formed during the incubation can be controlled, for example, by the temperature and time duration of the incubation, the concentration of pre-coated bead solution, and the density of molecule A 512 seeded on cover glass 510.

In FIG. 5D, once the sample is ready for measurement, it is loaded onto spinning force system 100. In this example, cover glass 510 is configured to be parallel to rotational axis 102 of system 100. The rotation of the sample therefore results in a centrifugal force F on bead 520, pulling it away in a direction perpendicular to the surface of cover glass 510. The movement of bead 520 can be monitored using one or more of the imaging techniques described above. When the magnitude of centrifugal force F is sufficiently high to rupture interaction 530, bead 520 is released from cover glass 510.

In this example, hundreds or thousands of molecular interactions 530 can be formed and observed in one experiment, allowing statistical analysis of such observations to be performed in a highly efficient manner.

3.2 Example II

Another application of spinning force system 100 relates to studying the intramolecular dynamics of a single molecule or a molecular tether (e.g., a protein or a DNA tether), including, for example, measuring the folding, unfolding, stretching, and relaxation of a molecular strand.

FIGS. 6A-6D illustrate use of system 100 in a procedure for preparing a sample containing a molecular tether to be measured.

In FIG. 5A, a cover glass 610 is coated with a dispersed layer of molecule A 612 using proper functionalization techniques such as physisorption.

In FIG. 6B, a solution of glass beads 620 and a solution of molecular tethers 630 (e.g., DNA tethers as shown in FIGS. 6B-6D for illustrative purposes) are added onto cover glass 610. Each bead 620 is pre-coated with one or more molecule A 612, and each molecular tether 630 is functionalized with one or more molecule B 632 capable of forming interactions with molecule A 612. Examples of commonly used functionalization techniques and procedures include silanization for glass substrate, formation of a peptide bond between a carboxylated surface and a free amine on a protein, and formation of disulfide bonds or S—C bonds for cysteine residues.

In FIG. 6C, cover glass 610 is incubated with glass beads 620 and molecular tether 630 to enable formation of interaction 640 between molecules A and B. Consequently, some beads 620 become attached to the surface of cover glass 610 through a newly formed interaction 640 between bead 620 and molecular tether 630 and another newly formed interaction 640' between molecular tether 630 and cover glass 610. Unattached beads can be removed from the surface by rinsing with an inactive solution, or alternatively, removed by a centrifugal force during measurement. In some examples, the amount of interactions 640 formed during incubation can be controlled, for example, by the temperature and time duration of incubation, the concentration of pre-coated bead solution and molecular tether solution, and the density of molecule A 612 seeded on cover glass 610.

In FIG. 6D, once the sample is ready for measurement, it is loaded onto spinning force system 100. For illustrative purposes, cover glass 610 is configured to be parallel to rotational axis 102 of system 100. The rotation of the sample therefore results in a centrifugal force F on bead 620, pulling it away in a direction perpendicular to the surface of cover glass 610.

The movement of bead 620 indicates the force-induced conformational changes of molecular tether 630 and can be used to measure variables characterizing the folding, unfolding, stretching and relaxation of the molecular tether in response to an external force. When the magnitude of F is varied (without exceeding the bond rupture force to break interaction 634), the force dependent dynamics of DNAs can also be quantified.

Again, in this example, hundreds or thousands of molecular tethers 630 can be studied in a single experiment, allowing statistical analysis of the results to be performed efficiently.

3.3 Example III

Another application of spinning force system 100 relates to studying the characteristics of molecules or molecular interactions in controlled chemical environments, including, for example, quantifying molecular dynamics at various temperatures, pH conditions, and/or salt concentrations, as well as in the presence of various kinds of surfactants and/or enzymes.

FIGS. 7A-7D illustrate use of system 100 in a procedure for preparing a sample containing a molecular tether 730 that can be modified by a restriction enzyme 760.

Figure 7B:
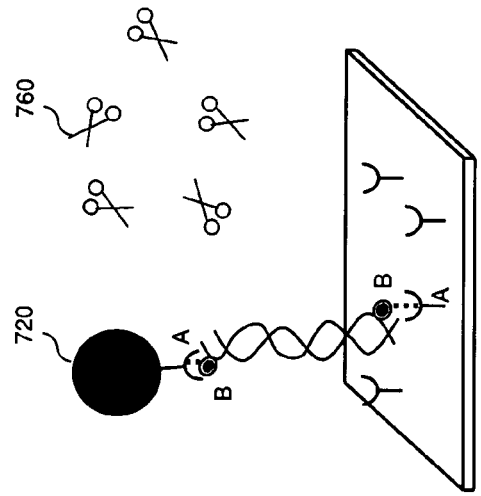
FIGS. 7A-7D are schematic representations of a further procedure for preparing a sample to be measured by the spinning force system of FIG. 1.
Figure 7D:
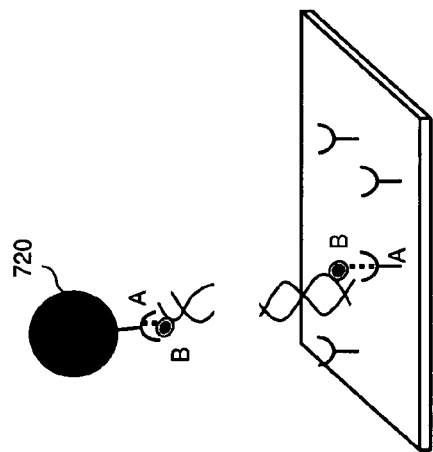
Figure 7A:
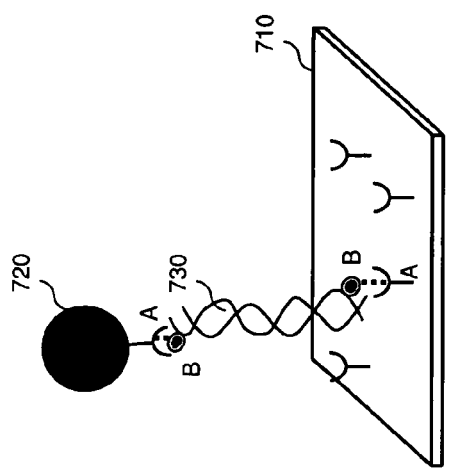

For example, in FIG. 7A, molecular tether 730 (e.g., a DNA strand) is attached to a cover glass 710 and a particle 720 using preparation techniques described above with reference to FIGS. 6A-6C.

In FIG. 7B, a solution of restriction enzymes 760 is added onto cover glass 710. Examples of restriction enzyme 760 include an enzyme that cuts double-stranded or single-stranded DNA at specific recognition nucleotide sequences (known as restriction sites). Restriction enzymes can be used for manipulating DNA in various applications such as DNA digestion and gene insertion.

Figure 7C:
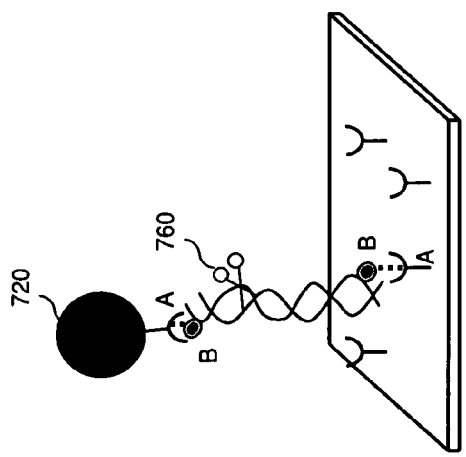

In FIG. 7C, molecular tether 730 is incubated in the solution of restriction enzymes 760 to allow one or more enzyme molecules to bind to the restriction sites of tether 730.

In FIG. 7D, upon binding with tether 730, restriction enzyme 760 makes incisions at selected locations in tether 730, cutting the tether into two or more disconnected pieces. As a result, particle 720 is released from the surface of cover glass 710. Particle release can be observed using the imaging techniques described above.

Some or all of the procedures shown in FIGS. 7A-7D may be performed during spinning. For example, the binding/interaction between tether 730 and restriction enzyme 760 may be monitored under the influence of a controlled centrifugal force applied to particle 720 as shown in FIG. 6D.

3.4 Example IV

Another application of spinning force system 100 relates to studying different types of molecular interactions and/or molecular dynamics in parallel. This application allows a direct comparison of molecular events of similar or different nature, such as the mobility of two different motor proteins, the compliance of various pieces of DNA strands, and the affinity of various receptor-ligand pairs. To distinguish the observations of motion characteristics resulted from distinct molecular events, each type of event can be uniquely labeled, for example, using fluorescent tracers or other kinds of markers. For example, in cases where two types of cytoskeletal proteins (e.g., microtubules and actin filaments) are studied at once, each type can be labeled by fluorescent beads of distinct emission wavelengths. By using selected optical filters to alternate observation of photons of different colors, the motion characteristics of each type of cytoskeletal proteins can be distinguished based on the resulting fluorescent images.

3.5 Example V

Although the previous examples are provided primarily in the context of measuring molecular dynamics or interactions, spinning force system 100 is also useful in measuring characteristics of interactions that occur on a cellular and/or tissue level. One example is to study the adhesion strength between adherent cells (e.g., endothelial or epithelial cells) and the underlying substrate or matrix to which the cells adhere. A monolayer of adherent cells can be seeded on a receptor-modified (e.g., fibronectin-coated) cover glass to form adhesion complexes (e.g., clusters of adhesion molecules such as integrins, syndecans, and cadherins). The cover glass is then mounted to rotary arm 120 and cells are monitored during rotation. The magnitude of centrifugal force that detaches cells from the cover glass indicates the maximum adhesion strength of the adhesion complexes.

3.6 Example VI

Another application of spinning force system 100 relates to using system 100 in conjunction with other detection or measurement techniques (e.g., various kinds of single-molecule force probes or fluidic systems) to obtain force-related characteristics of the sample. For example, system 100 can be combined with a magnetic system to apply both magnetic and centrifugal forces to manipulate a test subject. A biotin labeled magnetic bead can be first pulled by a magnetic force toward a cell membrane (or a streptavidin-treated surface) to form a biotin-streptavidin attachment. The strength of this attachment can then be tested by applying a centrifugal force that pulls the bead away from the membrane.

System 100 can also be combined in use with devices that apply various types of chemical stimuli (e.g., chemoattractants and enzymes) and mechanical stimuli (e.g., compression, extension, and shearing) to a test subject, simulating the native environment of the subject during observation. For example, when system 100 is used for measuring the mechanical properties (e.g., elasticity or viscoelasticity) of endothelial cells, during spinning, a laminar or cyclic shear stress may also be provided to mimic the conditions of the endothelial cells in vivo. Additionally, cellular response to chemical/mechanical stimuli may also be observed.

3.7 Other Examples

In addition to detecting characteristics of biomolecular or chemical interactions, system 100 is also suitable for use with a wide range of general testing tasks. Examples include 1) measuring the mechanical properties of polymer networks or aggregates, where the overall behavior of the network may be of interest; 2) testing the strength and other characteristics of physical bonds formed between a subject and a surface; and 3) observing the behavioral changes of test subjects effected by chemical agents (e.g., an enzyme slicing a single DNA between two surfaces or urea denaturing a protein).

4 Alternative Embodiments

Many variations of spinning force system 100 are possible.

Figure 8:
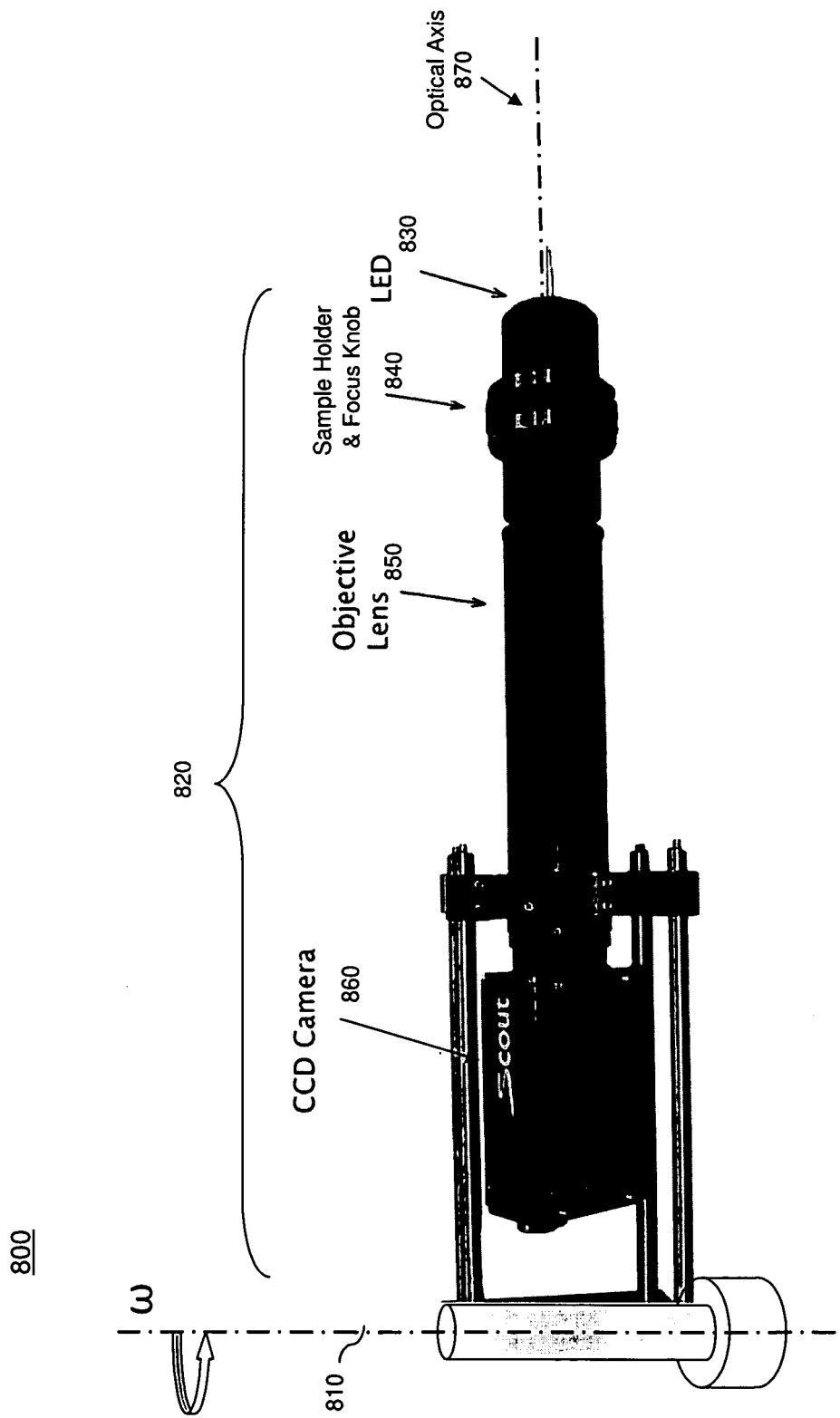
FIG. 8 shows an alternative embodiment (schematic in part) of the spinning force system of FIG. 1.

Referring to FIG. 8, an alternative embodiment of spinning force system 800 includes a coaxial detection assembly 820 mechanically coupled to a rotary stage 810. Detection assembly 820 includes a LED lamp 830, a sample holder 840, an objective lens 850, and a CCD camera 860, each being coaxially aligned with optical axis 870. LED lamp 830 is integrated into sample holder 840, which can be translated (e.g., along optical axis 870) through a focus knob for coarse adjustment. Fine adjustment of the position of sample holder 840 can be performed using a piezoelectric stage coupled to the holder (not shown). When rotary stage 810 operates in circular motion at angular velocity ω, the entire detection assembly 820 rotates at ω.

In some implementations, detection assembly 820 may be miniaturized to fit inside a standard centrifuge, eliminating the need for rotary stage 810 and reducing system cost.

Figure 9:
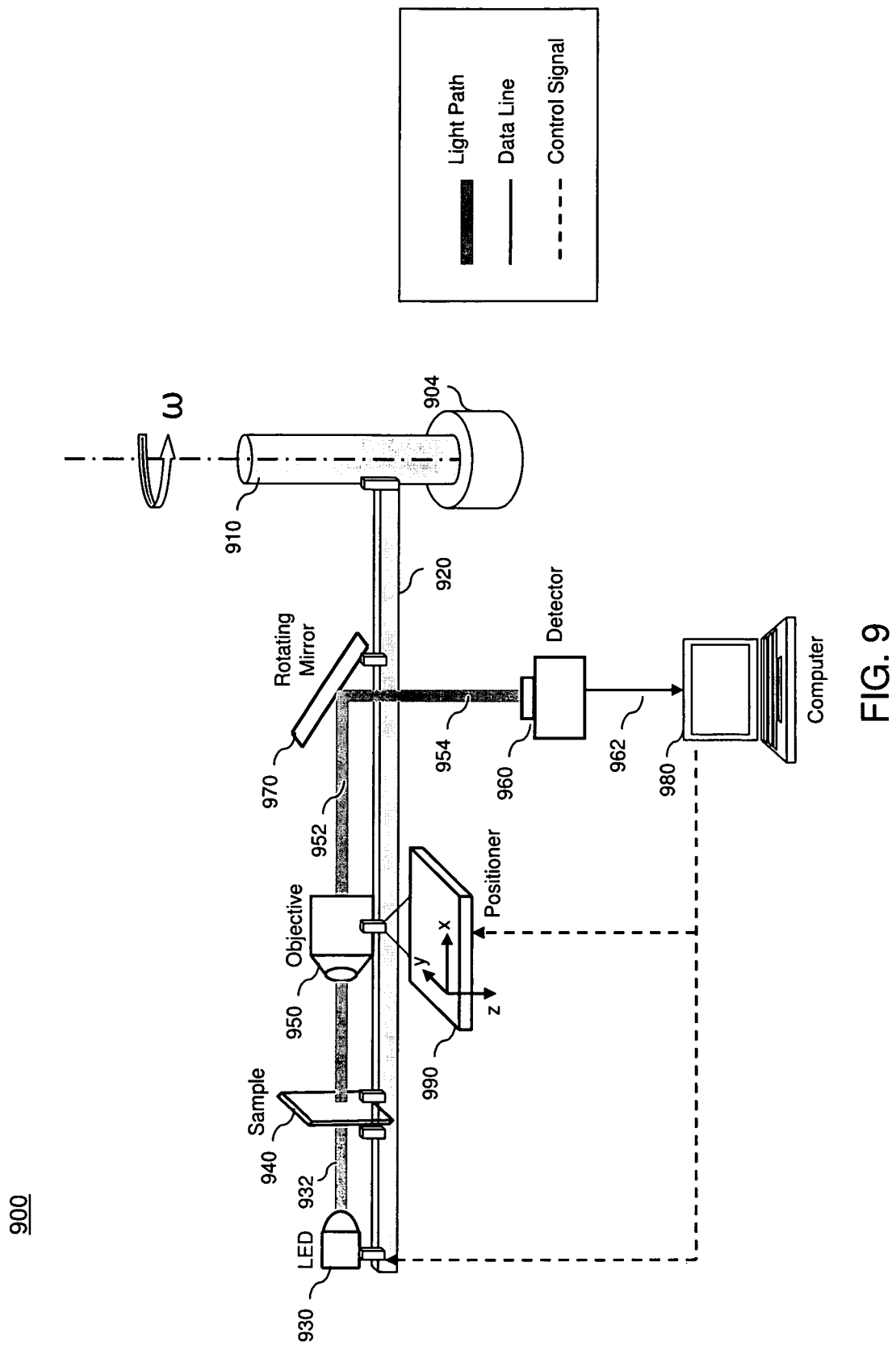
FIG. 9 shows an additional alternative embodiment of the spinning force system of FIG. 1.

Referring to FIG. 9, another alternative embodiment of spinning force system 900 is shown. Unlike detector 160 in system 100, detector 960 in this example is not mounted on rotary arm 920. Rather, detector 960 remains immobile during operation of system 900. Light from objective 950 are directed by a rotating mirror 970 to detector 960 through light paths 952 and 954 subsequently. Rotating mirror 970 is not necessarily mounted on rotary arm 920. For example, mirror 970 can be coupled to a separate rotor (not shown) or directly coupled to rotary stage 910 in order to reflect light from the rotating objective 950 to the stationary detector 960.

In the above examples of FIGS. 1, 8, and 9, the samples are detected using trans-illumination imaging techniques. More specifically, in FIG. 1, light 132 emitted from LED 130 transmits (penetrates) through sample 140 prior to being received by objective 150. In other examples, epi-illumination imaging techniques can also be conveniently used.

Figure 10:
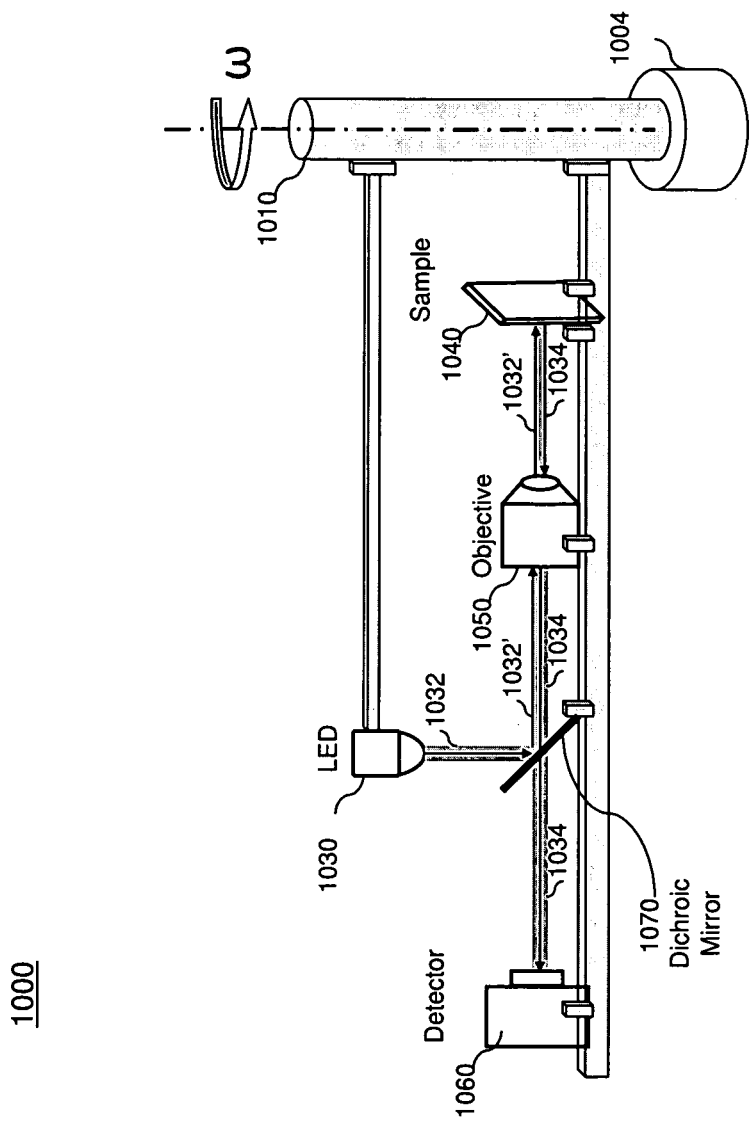
FIG. 10 shows a further alternative embodiment of the spinning force system of FIG. 1.

Referring to FIG. 10, a further alternative embodiment of spinning force system 1000 with epi-illumination is shown. Here, a Dichroic mirror 1070 is positioned between detector 1060 and objective 1050, serving as a beam splitter that directs light beams of different characteristics (e.g., different wavelengths) onto different paths. For example, light beam 1032 from LED 1030 is first deflected by Dichroic mirror 1070 towards objective 1050 (along light path 1032') to illuminate a selected region of sample 1040. A light beam 1034 is reflected from sample 1040 as a result of the illumination, travelling in a direction opposite to light beam 1032'. After passing through objective 1050 and Dicroic Mirror 1070, light beam 1034 is received by detector 1060 to produce an image of the illuminated region of sample 1040. In this example, objective 1050 serves as both a light condenser and an imaging lens.

In some embodiments, a vertical swinging or radially movable arm may be integrated to system 100 to enhance the flexibility of force control. System 100 may also be multiplexed to have many arms, each configured to carry a unique experiment. Each arm may also have a different and possibly adjustable length to facilitate force control.

It is to be understood that the foregoing description is intended to illustrate and not to limit the scope of the invention, which is defined by the scope of the appended claims. Other embodiments are within the scope of the following claims.

What is claimed is:
1. A method comprising:
   attaching a particle to a surface of a substrate through a molecular interaction associated with a first molecule and a second molecule;
   rotating the substrate to apply a force to the particle in a direction that is not in parallel to the surface of the substrate;

detecting an image of the particle with a detector during rotation of the substrate, the image containing information representing a characteristic of the molecular interaction; and determining the characteristic of the molecular interaction based on the detected image.

2. The method of claim 1, further comprising: detecting a relative motion of the particle to the surface of the substrate.

3. The method of claim 2, wherein the relative motion includes detachment of the particle from the surface of the substrate.

4. The method of claim 2, wherein the relative motion includes a motion indicative of a rupture or a formation of a chemical bond associated with the molecular interaction.

5. The method of claim 2, wherein the relative motion includes a motion indicative of a conformational change of at least one of the first and the second molecules.

6. The method of claim 5, wherein the conformational change includes any one or more of unfolding, refolding, stretching and relaxing of at least one of the first and second molecules.

7. The method of claim 1, wherein determining the characteristic of the molecular interaction includes measuring a strength characteristic of the molecular interaction.

8. The method of claim 1, wherein determining the characteristic of the molecular interaction includes measuring a kinetic characteristic of the molecular interaction.

9. The method of claim 8, wherein the kinetic characteristic of the molecular interaction includes an association rate $K_{on}$ or a dissociation rate $K_{off}$ of the molecular interaction.

10. The method of claim 1, further comprising forming a first chemical linkage between the particle and the first molecule.

11. The method of claim 1, further comprising forming a second chemical linkage between the second molecule and the surface of the substrate.

12. The method of claim 1, further comprising controlling a rotation of the substrate.

13. The method of claim 12, wherein controlling a rotation of the substrate further includes controlling an angular velocity of the rotation of the substrate.

14. The method of claim 1, wherein the first molecule is a receptor and the second molecule is a ligand of the receptor.

15. The method of claim 1, wherein the first molecule includes a first molecular complex, and the second molecule includes a second molecular complex that interacts with the first molecular complex.

16. The method of claim 15, wherein the first molecular complex includes one or more pairs of receptor and ligand.

17. The method of claim 1, wherein the particle includes a bead.

18. The method of claim 17, wherein the bead has a diameter in the range between 1 nm and 1 mm, and a density in the range between 0.01 g/cm$^3$ and 20 g/cm$^3$.

19. A method comprising:
attaching a particle to a surface of a substrate through a molecular interaction associated with a first molecule and a second molecule;
rotating the substrate to apply a force to the particle in a direction that is not in parallel to the surface of the substrate;
rotating at least a portion of a detection assembly with the substrate;
detecting an image of the particle with the detection assembly, the image containing information representing a characteristic of the molecular interaction; and
determining the characteristic of the molecular interaction based on the detected image.

20. The method of claim 19, wherein the detection assembly comprises a detector, and wherein the substrate is rotated relative to the detector.

21. A method comprising:
attaching a particle to a surface of a substrate through a molecular interaction associated with a first molecule and a second molecule;
rotating the substrate to apply a force to the particle in a direction that is not in parallel to the surface of the substrate;
detecting an image of the particle with a detector during an event associated with the molecular interaction, the event being caused by rotation of the substrate and the image containing information representing a characteristic of the molecular interaction; and
determining the characteristic of the molecular interaction based on the detected image.

22. The method of claim 21, wherein the event associated with the molecular interaction comprises detachment of the particle from the substrate.

23. The method of any one of claim 1, 19 or 21, wherein the molecular interaction is a molecular interaction between the first molecule and the second molecule.

24. The method of any one of claim 1, 19 or 21, wherein the molecular interaction is a molecular interaction within at least one of the first and second molecules.

25. The method of any one of claim 1, 19 or 21, wherein the characteristic of the molecular interaction is a rupture or a formation of a bond in at least one of the first and second molecules.

26. The method of claim 25, wherein the characteristic of the molecular interaction is a rupture or a formation of a bond in the presence of an enzyme.

27. The method of any one of claim 1, 19 or 21, wherein the characteristic of the molecular interaction is a conformational change of at least one of the first and second molecules.

28. The method of claim 27, wherein the conformational change includes any one or more of unfolding, refolding, stretching and relaxing of at least one of the first and second molecules.

29. The method of any one of claim 1, 19 or 21, wherein more than one image is detected.

30. The method of any one of claim 1, 19 or 21, wherein at least one of the first and second molecules is DNA.

31. The method of any one of claim 1, 19 or 21, wherein at least one of the first and second molecules is a protein.

32. A method comprising:
attaching a particle to a surface of a substrate, wherein the particle is attached to a first molecule;
rotating the substrate to apply a force to the particle in a direction that is not in parallel to the surface of the substrate;
detecting an image of the particle with a detector during rotation of the substrate, the image containing information representing a characteristic of the first molecule; and
determining the characteristic of the first molecule based on the detected image.

33. The method of claim 32, wherein the characteristic of the first molecule is a molecular interaction within the first molecule.

34. The method of claim 32, wherein the characteristic of the first molecule is a rupture or a formation of a bond in the first molecule.

35. The method of claim 32, wherein the characteristic of the first molecule is a rupture or a formation of a bond in the presence of an enzyme.

36. The method of claim 32, wherein the characteristic of the first molecule is a conformational change in the first molecule.

37. The method of claim 36, wherein the conformational change includes any one or more of unfolding, refolding, stretching and relaxing of the first molecule.

38. The method of claim 32, wherein more than one image is detected.

39. The method of claim 32, wherein the first molecule is DNA.

40. The method of claim 32, wherein the first molecule is a protein.

* * * * *

UNITED STATES PATENT AND TRADEMARK OFFICE
CERTIFICATE OF CORRECTION

| | | |
|---|---|---|
| PATENT NO. | : 8,491,454 B2 | Page 1 of 1 |
| APPLICATION NO. | : 12/326279 | |
| DATED | : July 23, 2013 | |
| INVENTOR(S) | : Wong et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1092 days.

Signed and Sealed this
Third Day of March, 2015

Michelle K. Lee
*Deputy Director of the United States Patent and Trademark Office*